United States Patent
Gray et al.

(10) Patent No.: US 9,265,855 B2
(45) Date of Patent: *Feb. 23, 2016

(54) FEMININE HYGIENE ABSORBENT ARTICLE COMPRISING A SUPERABSORBENT FOAM OF HIGH SWELL RATE

(75) Inventors: Brian Francis Gray, Cincinnati, OH (US); Achille Di Cintio, Pescara (IT); Giovanni Carlucci, Chieti (IT); Antje Ziemer, Mannheim (DE); Anna Kowalski, Frankenthal (DE); Ernst Juergen Bauer, Ludwigshafen (DE); Stefan Bruhns, Hellerup (DK)

(73) Assignee: The Procter & Gamble Company, Cincinnati, OH (US)

( * ) Notice: Subject to any disclaimer, the term of this patent is extended or adjusted under 35 U.S.C. 154(b) by 385 days.

This patent is subject to a terminal disclaimer.

(21) Appl. No.: 13/469,486

(22) Filed: May 11, 2012

(65) Prior Publication Data

US 2012/0296295 A1    Nov. 22, 2012

Related U.S. Application Data

(60) Provisional application No. 61/487,392, filed on May 18, 2011.

(51) Int. Cl.
| A61L 15/18 | (2006.01) |
| A61F 13/534 | (2006.01) |
| A61F 13/15 | (2006.01) |
| A61L 15/24 | (2006.01) |
| A61L 15/42 | (2006.01) |
| A61L 15/60 | (2006.01) |
| A61F 13/53 | (2006.01) |

(52) U.S. Cl.
CPC ........... *A61L 15/18* (2013.01); *A61F 13/15203* (2013.01); *A61F 13/534* (2013.01); *A61L 15/24* (2013.01); *A61L 15/425* (2013.01); *A61L 15/60* (2013.01); *A61F 2013/15373* (2013.01); *A61F 2013/15406* (2013.01); *A61F 2013/530226* (2013.01); *A61F 2013/530649* (2013.01); *A61F 2013/530693* (2013.01); *Y10T 428/233* (2015.01); *Y10T 428/237* (2015.01); *Y10T 428/239* (2015.01)

(58) Field of Classification Search
CPC ............. A61L 15/18; C08L 33/08; C08J 9/06
See application file for complete search history.

(56) References Cited

U.S. PATENT DOCUMENTS

| 5,118,719 | A | | 6/1992 | Lind |
| 5,352,711 | A | * | 10/1994 | DesMarais .................... 521/149 |
| 6,136,873 | A | | 10/2000 | Hähnle et al. |
| 6,310,113 | B1 | | 10/2001 | Reichman et al. |
| 2004/0157734 | A1 | * | 8/2004 | Mertens et al. ............... 502/401 |
| 2005/0176834 | A1 | * | 8/2005 | Hintz et al. ..................... 521/50 |
| 2005/0228350 | A1 | * | 10/2005 | Ranganathan et al. ............... A61F 13/47263 604/367 |
| 2006/0029782 | A1 | * | 2/2006 | Harren et al. ................. 428/212 |
| 2008/0214740 | A1 | * | 9/2008 | Harren et al. ................. 525/281 |
| 2009/0045138 | A1 | * | 2/2009 | Champ et al. ................. 210/689 |
| 2010/0268181 | A1 | | 10/2010 | Ziemer et al. |
| 2012/0295090 | A1 | * | 11/2012 | Ziemer et al. ................. 428/220 |
| 2012/0296296 | A1 | * | 11/2012 | Di Cintio et al. ............. 604/369 |
| 2012/0296297 | A1 | | 11/2012 | Di Cintio et al. |
| 2012/0296298 | A1 | | 11/2012 | Gray et al. |
| 2014/0158626 | A1 | * | 6/2014 | Ziemer et al. ................. 210/660 |

FOREIGN PATENT DOCUMENTS

GB          2136813          9/1984

OTHER PUBLICATIONS

PCT International Search Report, mailed Jul. 5, 2012, 6 pages.

* cited by examiner

*Primary Examiner* — Hai Vo
(74) *Attorney, Agent, or Firm* — Andres E. Velarde; Amanda T. Barry

(57) ABSTRACT

This invention relates to a feminine hygiene absorbent article comprising superabsorbent foams obtainable by foaming an aqueous mixture comprising at least one monoethylenically unsaturated monomer bearing acid groups, at least one blowing agent, at least one crosslinker and at least one surfactant, polymerizing the foamed mixture and drying the polymerized mixture, to the foams and also to their use for absorbing aqueous fluids.

16 Claims, No Drawings

FEMININE HYGIENE ABSORBENT ARTICLE COMPRISING A SUPERABSORBENT FOAM OF HIGH SWELL RATE

CROSS REFERENCE TO RELATED APPLICATION(S)

This application claims the benefit of U.S. Provisional Application No. 61/487,392, filed May 18, 2011.

FIELD OF THE INVENTION

This invention relates to a feminine hygiene absorbent article comprising superabsorbent foams obtainable by foaming an aqueous mixture comprising at least one monoethylenically unsaturated monomer bearing acid groups, at least one blowing agent, at least one crosslinker and at least one surfactant, polymerizing the foamed mixture and drying the polymerized mixture, to the foams and also to their use for absorbing aqueous fluids.

Further embodiments of the present invention are discernible from the claims, the description and the examples. It will be appreciated that the hereinabove identified and the hereinbelow still to be more particularly described features of the subject matter of the present invention are utilizable not just in the particular combination indicated but also in other combinations without leaving the realm of the present invention.

BACKGROUND OF THE INVENTION

Superabsorbent foams based on crosslinked monomers comprising acid groups are known, cf. EP 858 478 B1, WO 97/31971 A1, WO 99/44648 A1 and WO 00/52087 A1. They are produced for example by foaming a polymerizable aqueous mixture comprising not less than 50 mol % neutralized acid-functional monoethylenically unsaturated monomers, crosslinkers and at least one surfactant and then polymerizing the foamed mixture. The foaming of the polymerizable mixture can be effected for example by dispersing fine bubbles of a gas which is inert toward free radicals or by dissolving such a gas in the polymerizable mixture under elevated pressure and depressurizing the mixture. The water content of the foams is set in the range from 1% to 60% by weight for example. The foams may be subjected to surface-post-crosslinking, if appropriate, by spraying a crosslinker onto the foamed material or dipping the foam into the cross-linker and heating the crosslinker-laden foam to a higher temperature. The foams are used for example in hygiene articles to acquire, distribute and store body fluids.

WO 03/066717 A2 discloses a process whereby wet strength is enhanced and residual monomer content lowered for superabsorbent foams by addition of amino-comprising polymers.

WO 2004/007598 A1 discloses water-absorbing foams comprising finely divided hydrophilic silicon dioxide and/or a surfactant at the surface. The treatment of the foams leads to an increase in the takeup rate for liquids.

WO 2004/035668 A2 discloses water-absorbing foams comprising superabsorbent fibers or fruit fibers, in particular apple fibers.

WO 2006/094977 A2 describes superabsorbent foams comprising wood fibers or waste paper fibers.

WO 2005/042039 A2 describes superabsorbent foams possessing enhanced blood absorbence due to their being coated with hydrophobic compounds.

The present invention has for its object to improve the properties of feminine hygiene absorbent articles comprising superabsorbent foams, in particular by providing foams that have good absorbing, retaining and conducting properties for aqueous fluids and are stable, in particular in the wet state, efficiently handleable, efficiently processable and simple to produce.

SUMMARY OF THE INVENTION

We have found that this object is achieved according to the present invention by a feminine hygiene absorbent article comprising a superabsorbent foam obtainable by foaming an aqueous mixture comprising at least one monoethylenically unsaturated monomer bearing acid groups, at least one crosslinker and at least one surfactant, polymerizing the foamed mixture and drying the polymerized mixture, wherein the foamed mixture comprises at least 1% by weight, based on the monomer, of at least one compound capable of thermal decomposition with gas formation.

DETAILED DESCRIPTION OF THE INVENTION

The term "feminine hygiene absorbent article" is used herein in a broad sense including any article able to receive and/or absorb and/or contain and/or retain body fluids/bodily exudates such as menses, vaginal secretions, and urine. Exemplary feminine hygiene absorbent articles in the context of the present invention are disposable feminine hygiene absorbent articles. The term "disposable" is used herein to describe articles, which are not intended to be laundered or otherwise restored or reused as an article (i.e. they are intended to be discarded after a single use and preferably to be recycled, composted or otherwise disposed of in an environmentally compatible manner). Typical disposable feminine hygiene absorbent articles according to the present invention are sanitary napkins, panty liners, tampons, absorbent articles for low or moderate incontinence or the like. Absorbent articles suitable for use in the present invention include any type of structures, from a single absorbent layer to more complex multi layer structures. Certain absorbent articles typically include a fluid pervious topsheet, a backsheet, which may be fluid impervious and/or may be water vapour and/or gas pervious, and an absorbent element often called "core" comprised there between.

Absorbent articles according to the present invention can typically comprise a topsheet, a backsheet and an absorbent core.

The topsheet may be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be included of natural fibers (e.g., wood or cotton fibers), synthetic fibers (e.g., polymeric fibers such as polyester, polypropylene, or polyethylene fibers) or from a combination of natural and synthetic fibers. In one embodiment, the topsheet may be made of a hydrophobic material to isolate the wearer's skin from liquids which have passed through the topsheet. If the topsheet is made of a hydrophobic material, at least the upper surface of the topsheet is treated to be hydrophilic so that liquids will transfer through the topsheet more rapidly. This diminishes the likelihood that body exudates will flow off the topsheet rather than being drawn through the topsheet and being absorbed by the absorbent core. In one embodiment, the topsheet can be rendered hydrophilic by treating it with a surfactant. Suitable methods for treating the topsheet with a surfactant include spraying the topsheet material with the surfactant and immersing the material into the surfactant.

For example, the topsheet can be a nonwoven web that can provide reduced tendency for surface wetness; and consequently facilitate maintaining body fluids absorbed by the core away from the user's skin, after wetting. One suitable topsheet material can be a thermobonded carded web which is available as Code No. P-8 from Fiberweb North America, Inc. (Simpsonville, S.C., U.S.A.). Another suitable topsheet material is available as Code No. S-2355 from Havix Co., Japan. Yet another suitable topsheet material can be a thermobonded carded web which is available as Code No. Profleece Style 040018007 from Amoco Fabrics, Inc. (Gronau, Germany).

The topsheet can include an apertured formed film. Apertured formed films can be used for the topsheet because they are pervious to body exudates and yet non-absorbent and have a reduced tendency to allow liquids to pass back through and rewet the wearer's skin. Thus, the surface of the formed film which is in contact with the body remains dry, thereby reducing body soiling and creating a more comfortable feel for the wearer. Suitable formed films are described in U.S. Pat. No. 3,929,135, entitled "Absorptive Structures Having Tapered Capillaries", issued to Thompson on Dec. 30, 1975; U.S. Pat. No. 4,324,246 entitled "Disposable Absorbent Article Having A Stain Resistant Topsheet", issued to Mullane, et al. on Apr. 13, 1982; U.S. Pat. No. 4,342,314 entitled "Resilient Plastic Web Exhibiting Fiber-Like Properties", issued to Radel, et al. on Aug. 3, 1982; U.S. Pat. No. 4,463,045 entitled "Macroscopically Expanded Three-Dimensional Plastic Web Exhibiting Non-Glossy Visible Surface and Cloth-Like Tactile Impression", issued to Ahr, et al. on Jul. 31, 1984; and U.S. Pat. No. 5,006,394 "Multilayer Polymeric Film" issued to Baird on Apr. 9, 1991.

The absorbent core can be any absorbent member which is generally compressible, conformable, non-irritating to the wearer's skin, and capable of absorbing and retaining body fluids. The absorbent core may be manufactured in a wide variety of sizes and shapes (e.g., rectangular, hourglass, "T"-shaped, asymmetric, etc.) and from a wide variety of liquid-absorbent materials commonly used in disposable pull-on garments and other absorbent articles such as comminuted wood pulp which is generally referred to as airfelt. Examples of other suitable absorbent materials include creped cellulose wadding; meltblown polymers including coform; chemically stiffened, modified or cross-linked cellulosic fibers; tissue including tissue wraps and tissue laminates; absorbent foams; absorbent sponges; superabsorbent polymers; absorbent gelling materials; or any equivalent material or combinations of materials.

The configuration and construction of the absorbent core may vary (e.g., the absorbent core may have varying caliper zones, a hydrophilic gradient, a superabsorbent gradient, or lower average density and lower average basis weight acquisition zones; or may include one or more layers or structures). Further, the size and absorbent capacity of the absorbent core may also be varied to accommodate wearers ranging from infants through adults. However, the total absorbent capacity of the absorbent core should be compatible with the design loading and the intended use of the absorbent article.

The absorbent core may include other optional components. One such optional component is the core wrap, i.e., a material, typically but not always a nonwoven material, which either partially or totally surrounds the core. Suitable core wrap materials include, but are not limited to, cellulose, hydrophilically modified nonwoven materials, perforated films and combinations thereof.

The backsheet can comprise a liquid impervious film. The backsheet can be impervious to liquids (e.g., body fluids) and can be typically manufactured from a thin plastic film. However, typically the backsheet can permit vapours to escape from the disposable article. In an embodiment, a microporous polyethylene film can be used for the backsheet. A suitable microporous polyethylene film is manufactured by Mitsui Toatsu Chemicals, Inc., Nagoya, Japan and marketed in the trade as PG-P.

One suitable material for the backsheet can be a liquid impervious thermoplastic film having a thickness of from about 0.012 mm (0.50 mil) to about 0.051 mm (2.0 mils), for example including polyethylene or polypropylene. Typically, the backsheet can have a basis weight of from about 5 g/m2 to about 35 g/m2. However, it should be noted that other flexible liquid impervious materials may be used as the backsheet. Herein, "flexible" refers to materials which are compliant and which will readily conform to the general shape and contours of the wearer's body.

The backsheet can be typically positioned adjacent the outer-facing surface of the absorbent core and can be joined thereto by any suitable attachment means known in the art. For example, the backsheet may be secured to the absorbent core by a uniform continuous layer of adhesive, a patterned layer of adhesive, or an array of separate lines, spirals, or spots of adhesive. Illustrative, but nonlimiting adhesives, include adhesives manufactured by H. B. Fuller Company of St. Paul, Minn., U.S.A., and marketed as HL-1358J. An example of a suitable attachment means including an open pattern network of filaments of adhesive is disclosed in U.S. Pat. No. 4,573,986 entitled "Disposable Waste-Containment Garment", which issued to Minetola et al. on Mar. 4, 1986. Another suitable attachment means including several lines of adhesive filaments swirled into a spiral pattern is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Alternatively, the attachment means may include heat bonds, pressure bonds, ultrasonic bonds, dynamic mechanical bonds, or any other suitable attachment means or combinations of these attachment means as are known in the art.

The backsheet may be additionally secured to the topsheet by any of the above-cited attachment means.

The absorbent article may also include such other features as are known in the art including, but not limited to, re-closable fastening system, lotion, acquisition layers, distribution layers, wetness indicators, sensors, elasticized waist bands and other similar additional elastic elements and the like, belts and the like, waist cap features, containment and aesthetic characteristics and combinations thereof.

According to the present invention, the feminine hygiene absorbent article can be a sanitary napkin, or a pantiliner, or a tampon, or an article for low or moderate adult incontinence. For example, the feminine hygiene absorbent article of the present invention can be a sanitary napkin or a pantiliner.

The feminine hygiene absorbent article of the present invention typically comprises a superabsorbent foam obtainable by foaming an aqueous mixture comprising at least one monoethylenically unsaturated monomer bearing acid groups, at least one crosslinker and at least one surfactant, polymerizing the foamed mixture and drying the polymerized mixture, wherein the foamed mixture comprises at least 1% by weight, based on the monomer, of at least one compound capable of thermal decomposition with gas formation.

The compounds capable of thermal decomposition with gas formation are not subject to any restriction. Examples of suitable compounds are urea, azo compounds, such as azodicarbonamide, and/or ammonium salts, such as ammonium bicarbonate. Urea, azodicarbonamide and/or ammonium bicarbonate are preferred. Urea is particularly preferred.

Superabsorbent foams are known from the prior art. Superabsorbent foam herein refers to a foam which has a centrifuge retention capacity (CRC, method of measurement described hereinbelow in the "Methods of determination" section) of at least 3 g/g, preferably at least 4 g/g, more preferably at least 5 g/g and especially at least 6 g/g.

Superabsorbent foams are conveniently obtainable by foaming an aqueous mixture comprising at least one monoethylenic unsaturated monomer bearing acid groups, the monomer being optionally at least partially neutralized, at least one crosslinker and at least one surfactant and also optionally additives or auxiliaries, such as solubilizers, thickeners, stabilizers, fillers, fibers and/or cell nucleators, and polymerizing.

One embodiment of the present invention comprises foaming an aqueous mixture comprising for example a) 10% to 95% by weight of monoethylenically unsaturated monomers which comprise acid groups and are at least 10 mol % neutralized, b) 0.8% to 24% by weight of at least one compound capable of thermal decomposition with gas formation, c) optionally in addition up to 50% by weight of other monoethylenically unsaturated monomers, d) 0.001% to 20% by weight of crosslinker, e) initiators, f) 0.01% to 20% by weight of at least one surfactant, g) optionally a solubilizer and h) optionally thickeners, foam stabilizers, polymerization regulators, fillers, fibers and/or cell nucleators, all based on the total amount of the mixture. This aqueous polymerizable mixture may also be called "monomer mixture" or "monomer solution".

The foaming of the aqueous mixtures can be effected for example by dispersing in the mixture fine bubbles of a gas which is inert toward free radicals, or by dissolving such a gas in the polymerizable mixture at a pressure in the range from 2 to 400 bar and subsequently decompressing the mixture to atmospheric. This provides a flowable foam which can be filled into molds or cured on a belt. Curing is effected by addition polymerization.

Suitable monomers a) are for example ethylenically unsaturated carboxylic acids, such as acrylic acid, methacrylic acid, maleic acid, fumaric acid and itaconic acid. Acrylic acid and methacrylic acid are particularly preferred monomers. Acrylic acid is most preferable.

The proportion of acrylic acid and/or salts thereof in the total amount of monomers a) is preferably at least 50 mol %, more preferably at least 90 mol %, most preferably at least 95 mol %.

The monomers a) and especially acrylic acid comprise preferably up to 0.025% by weight of a hydroquinone half ether. Preferred hydroquinone half ethers are hydroquinone monomethyl ether (MEHQ) and/or tocopherols.

Tocopherol refers to compounds of the following formula:

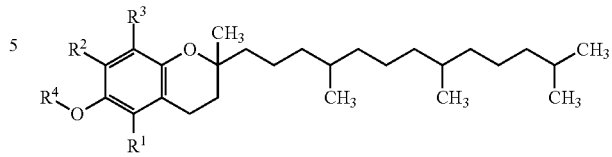

where $R^1$ is hydrogen or methyl, $R^2$ is hydrogen or methyl, $R^3$ is hydrogen or methyl and $R^4$ is hydrogen or an acid radical of 1 to 20 carbon atoms.

Preferred $R^4$ radicals are acetyl, ascorbyl, succinyl, nicotinyl and other physiologically tolerable carboxylic acids. The carboxylic acids can be mono-, di- or tricarboxylic acids.

Preference is given to alpha-tocopherol where $R^1=R^2=R^3=$methyl, especially racemic alpha-tocopherol. $R^4$ is more preferably hydrogen or acetyl. RRR-alpha-Tocopherol is preferred in particular.

The monomer solution comprises generally up to about 200 ppm, preferably not more than 130 weight ppm, more preferably not more than 70 weight ppm, preferably not less than 10 weight ppm, more preferably not less than 30 weight ppm and especially about 50 weight ppm of hydroquinone half ether, all based on acrylic acid, with acrylic acid salts being arithmetically counted as acrylic acid. For example, the monomer solution can be produced using an acrylic acid having an appropriate hydroquinone half ether content.

The acid groups of the monomers a) have typically been neutralized to an extent of 25 to 95 mol %, preferably to an extent of 40 to 85 mol %, more preferably to an extent of 50 to 80 mol %, especially preferably to an extent of 55 to 75 mol %, for which the customary neutralizing agents can be used, examples being alkali metal hydroxides, alkali metal oxides, alkali metal carbonates or alkali metal bicarbonates and also mixtures thereof.

Neutralization can also be effected with ammonia, amines or alkanolamines, such as ethanolamine, diethanolamine or triethanolamine, however. Preferred neutralizing agents are tertiary alkanolamines, such as triethanolamine, methyldiethanolamine, dimethylaminodiglycol, dimethylethanolamine and N,N,N',N'-tetra(hydroxyethyl)ethylenediamine. The preferred neutralizing agents can also be used in admixture with further neutralizing agents.

In a preferred embodiment of the present invention, 10 to 90 mol %, preferably 20 to 80 mol %, more preferably 30 to 70 mol %, most preferably 40 to 60 mol %, of the neutralized monomers a) have been neutralized by means of an alkanolamine.

With a rising proportion of alkanolamine, both the flexibility of the polymeric foams and the extractables content increase.

The amount of monomer a) is preferably 20 to 90% by weight, more preferably 30 to 85% by weight, most preferably 35 to 75% by weight, based in each case on the unneutralized monomer a) and on the monomer solution or suspension. Based on the unneutralized monomer a) means in the context of this invention that the proportion of the monomer a) before the neutralization is used for the calculation, i.e. the contribution of the neutralization is not taken into account.

The amount of compound capable of thermal decomposition with gas formation is typically 1% to 30% by weight, preferably 2% to 25% by weight, more preferably 3% to 20% by weight, even more preferably 4% to 15% by weight and most preferably 5% to 10% by weight, all based on the amount of monomer a). Further, if the compound capable of thermal decomposition with gas formation is urea, the amount of urea b) in the monomer solution is preferably in the range from 1.6% to 25% by weight, more preferably in the range from 2.4% to 20% by weight, even more preferably in the range from 3.2% to 15% by weight and most preferably in the range from 4% to 8% by weight.

Monomers c) are ethylenically unsaturated monomers that are copolymerizable with the monomers a), examples being acrylamide, methacrylamide, crotonamide, dimethylaminoethyl methacrylate, dimethylaminoethyl acrylate, dimethylaminopropyl acrylate, diethylaminopropyl acrylate, dimethylaminobutyl acrylate, dimethylaminoethyl methacrylate, diethylaminoethyl methacrylate, dimethylaminoneopentyl acrylate and dimethylaminoneopentyl methacrylate.

Crosslinkers d) are compounds having at least two polymerizable groups which can be free-radically interpolymerized into the polymer network. Useful crosslinkers d) include for example ethylene glycol dimethacrylate, diethylene glycol diacrylate, allyl methacrylate, trimethylolpropane triacrylate, triallylamine, tetraallyloxyethane as described in EP 530 438 A1, di- and triacrylates as described in EP 547 847 A1, EP 559 476 A1, EP 632 068 A1, WO 93/21237 A1, WO 03/104299 A1, WO 03/104300 A1, WO 03/104301 A1 and DE 103 31 450 A1, mixed acrylates which, as well as acrylate groups, comprise further ethylenically unsaturated groups, as described in DE 103 31 456 A1 and DE 103 55 401 A1, or crosslinker mixtures as described for example in DE 195 43 368 A1, DE 196 46 484 A1, WO 90/15830 A1 and WO 02/32962 A2.

Useful crosslinkers d) include in particular N,N'-methylenebisacrylamide and N,N'-methylenebismethacrylamide, esters of unsaturated mono- or polycarboxylic acids of polyols, such as diacrylate or triacrylate, for example butanediol diacrylate, butanediol dimethacrylate, ethylene glycol diacrylate, ethylene glycol dimethacrylate and also trimethylolpropane triacrylate and allyl compounds, such as allyl(meth)acrylate, triallyl cyanurate, diallyl maleate, polyallyl esters, tetraallyloxyethane, triallylamine, tetraallylethylenediamine, allyl esters of phosphoric acid and also vinylphosphonic acid derivatives as described for example in EP 343 427 A2. Useful crosslinkers d) further include pentaerythritol diallyl ether, pentaerythritol triallyl ether, pentaerythritol tetraallyl ether, polyethylene glycol diallyl ether, ethylene glycol diallyl ether, glycerol diallyl ether, glycerol triallyl ether, polyallyl ethers based on sorbitol, and also ethoxylated variants thereof. The process of the present invention may utilize di(meth)acrylates of polyethylene glycols, the polyethylene glycol used having a molecular weight between 300 and 1000.

However, particularly advantageous crosslinkers d) are di- and triacrylates of 3- to 20-tuply ethoxylated glycerol, of 3- to 20-tuply ethoxylated trimethylolpropane, of 3- to 20-tuply ethoxylated trimethylolethane, especially di- and triacrylates of 2- to 6-tuply ethoxylated glycerol or of 2- to 6-tuply ethoxylated trimethylolpropane, of 3-tuply propoxylated glycerol, of 3-tuply propoxylated trimethylolpropane, and also of 3-tuply mixedly ethoxylated or propoxylated glycerol, of 3-tuply mixedly ethoxylated or propoxylated trimethylolpropane, of 15-tuply ethoxylated glycerol, of 15-tuply ethoxylated trimethylolpropane, of at least 40-tuply ethoxylated glycerol, of at least 40-tuply ethoxylated trimethylolethane and also of at least 40-tuply ethoxylated trimethylolpropane.

Very particularly preferred for use as crosslinkers d) are diacrylated, dimethacrylated, triacrylated or trimethacrylated multiply ethoxylated and/or propoxylated glycerols as described for example in WO 03/104301 A1. Di- and/or triacrylates of 3- to 10-tuply ethoxylated glycerol are particularly advantageous. Very particular preference is given to di- or triacrylates of 1- to 5-tuply ethoxylated and/or propoxylated glycerol. The triacrylates of 3- to 5-tuply ethoxylated and/or propoxylated glycerol are most preferred.

The amount of crosslinker d) is preferably 0.5 to 15% by weight, more preferably 2 to 10% by weight and most preferably 3 to 8% by weight, based in each case on the unneutralized monomer a). With rising crosslinker content, the centrifuge retention capacity (CRC) falls and the absorption capacity under a pressure typically passes through a maximum.

Useful initiators e) for the polymerization reaction include all compounds that disintegrate into free radicals under the polymerization conditions, examples being peroxides, hydroperoxides, hydrogen peroxide, persulfates, azo compounds and the so-called redox catalysts, and also any other known method for generating free radicals, examples being high energy radiation, such as UV light for example. The use of water-soluble initiators or UV light is preferred. It is advantageous in some cases to use mixtures of various polymerization initiators, examples being mixtures of hydrogen peroxide and sodium or potassium peroxodisulfate. Mixtures of hydrogen peroxide and sodium peroxodisulfate can be used in any desired ratio. Suitable organic peroxides are for example acetylacetone peroxide, methyl ethyl ketone peroxide, tert-butyl hydroperoxide, cumene hydroperoxide, tert-amyl perpivalate, tert-butyl perpivalate, tert-butyl permeohexanoate, tert-butyl perisobutyrate, tert-butyl per-2-ethylhexanoate, tert-butyl perisononanoate, tert-butyl permaleate, tert-butyl perbenzoate, di-(2-ethylhexyl)peroxidicarbonate, dicyclohexyl peroxidicarbonate, di-(4-tert-butylcyclohexyl)peroxidicarbonate, dimyristil peroxidicarbonate, diacetyl peroxidicarbonate, allyl peresters, cumyl peroxyneodecanoate, tert-butyl per-3,5,5-trimethylhexa-noate, acetylcyclohexylsulfonyl peroxide, dilauryl peroxide, dibenzoyl peroxide and tert-amyl perneodecanoate. Particularly suitable polymerization initiators e) are azo initiators, for example 2,2'-azobis(2-amidinopropane)dihydrochloride, 2,2'-azobis(N,N-dimethylene)isobutyl-ramidine dihydrochloride, 2-(carbamoylazo)isobutyronitrile, 2,2'-azobis[2-(2'-imidazolin-2-yl)-propane]dihydrochloride and 4,4'-azobis(4-cyanovaleric acid). The polymerization initiators mentioned are used in customary amounts, generally at least 0.01 mol %, preferably at least 0.05 mol % and also more preferably at least 1 mol % and also generally not more than 5 mol % and preferably not more than 2 mol %, based on the monomers to be polymerized.

The redox catalysts comprise, as oxidizing component, at least one of the above-indicated per compounds and, as reducing component, for example ascorbic acid, glucose, sorbose, ammonium bisulfite, ammonium sulfite, ammonium thiosulfate, ammonium hyposulfite, ammonium pyrosulfite, ammonium sulfide, alkali metal bisulfite, alkali metal sulfite, alkali metal thiosulfate, alkali metal hyposulfite, alkali metal pyrosulfite, alkali metal sulfide, metal salts, such as iron(II) ions or silver ions or sodium hydroxymethylsulfoxylate. The reducing component of the redox catalyst is preferably ascorbic acid, sodium sulfite or sodium pyrosulfite. Generally from $3 \cdot 10^6$ mol % and preferably at least $1 \cdot 10^{-5}$ to 1 mol % of the reducing component of the redox initiator and generally at least $1 \cdot 10^{-5}$ mol % and preferably at least $1 \cdot 10^{-3}$ to 5 mol % of the oxidizing component are used based on the amount of monomers used in the polymerization. Instead of the oxidizing component or in addition it is also possible to use one or more water-soluble azo initiators.

One embodiment of the present invention utilizes a redox initiator consisting of hydrogen peroxide, sodium peroxodisulfate and ascorbic acid. These components are used for example in the concentrations of $1\text{-}10^{-2}$ mol % of hydrogen peroxide, 0.084 mol % of sodium peroxodisulfate and $2.5\text{-}10^{-3}$ mol % of ascorbic acid, based on the monomers.

However, the polymerization can also be started in the absence of initiators of the abovementioned kind through the action of high energy radiation in the presence of photoinitiators. These may be for example what are known as α-splitters, H-radiating systems or else azides. Examples of such initiators are benzophenone derivatives such as Michler's ketone, phenanthrene derivatives, fluorene derivatives, anthraquinone derivatives, thioxanthone derivatives, coumarin derivatives, benzoin ethers and derivatives thereof, azo compounds such as the free-radical formers mentioned above, substituted hexaarylbisimidazoles or acylphosphine oxides. Examples of azides are: 2-(N,N-dimethylamino)ethyl 4-azidocinnamate, 2-(N,N-dimethylamino)ethyl 4-azidonaphthyl ketone, 2-(N,N-dimethylamino)ethyl 4-azidobenzoate, 5-azido-1-naphthyl 2'-(N,N-dimethylamino)ethyl sulfone, N-(4-sulfonylazidophenyl)maleimide, N-acetyl-4-sulfonyl-azi-doaniline, 4-sulfonylazidoaniline, 4-azidoaniline, 4-azidophenacyl bromide, p-azidobenzoic acid, 2,6-bis(p-azidobenzylidene)cyclohexanone and 2,6-bis(p-azidobenzylidene)-4-methylcy-clo-hexanone.
Photoinitiators, if used, are typically used in amounts from 0.001% to 5% by weight, preferably 0.001 to 2% by weight, more preferably 0.01 to 1% by weight, most preferably 0.05 to 0.2% by weight, based in each case on the unneutralized monomer a) to be polymerized.

The aqueous monomer solution may comprise the initiator in dissolved or dispersed form. However, the initiators may also be added to the polymerization reactor separately from the monomer solution.

The polymerizable aqueous mixtures comprise at least one surfactant f) as a further component. The surfactants f) are of decisive importance for forming and stabilizing the foam. It is possible to use anionic, cationic or nonionic surfactants or surfactant mixtures which are compatible with each other. It is possible to use low molecular weight or else polymeric surfactants, and combinations of different or else similar types of surfactants have been determined to be advantageous. Examples of nonionic surfactants are addition products of alkylene oxides, especially ethylene oxide, propylene oxide and/or butylene oxide, with alcohols, amines, phenols, naphthols or carboxylic acids. The surfactants used are advantageously addition products of ethylene oxide and/or propylene oxide with alcohols comprising at least 10 carbon atoms, the addition products comprising from 3 to 200 mol of ethylene oxide and/or propylene oxide per mole of alcohol. The alkylene oxide units are present in the addition products in the form of blocks or in random distribution. Examples of useful nonionic surfactants are the addition products of 7 mol of ethylene oxide with 1 mol of tallow fat alcohol, reaction products of 9 mol of ethylene oxide with 1 mol of tallow fat alcohol and addition products of 80 mol of ethylene oxide with 1 mol of tallow fat alcohol. Further useful commercially available nonionic surfactants comprise reaction products of oxo process alcohols or Ziegler alcohols with from 5 to 12 mol of ethylene oxide per mole of alcohol, especially with 7 mol of ethylene oxide. Further useful commercially available nonionic surfactants are obtained by ethoxylation of castor oil. The amount of ethylene oxide added per mole of castor oil is for example in the range from 12 to 80 mol. Further useful commercially available products are for example the reaction products of 18 mol of ethylene oxide with 1 mol of tallow fat alcohol, the addition products of 10 mol of ethylene oxide with 1 mol of a $C_{13}/C_{15}$ oxo process alcohol or the reaction products of from 7 to 8 mol of ethylene oxide with 1 mol of a $C_{13}/C_{15}$ oxo process alcohol. Useful nonionic surfactants further include phenol alkoxylates such as for example p-tert-butylphenol which has been reacted with 9 mol of ethylene oxide or methyl ethers of reaction products of 1 mol of a $C_{12}$-$C_{18}$ alcohol and 7.5 mol of ethylene oxide.

The nonionic surfactants described above, for example by esterification with sulfuric acid, can be converted into the corresponding acid sulfuric esters. The acid sulfuric esters are used in the form of their alkali metal or ammonium salts as anionic surfactants. Useful anionic surfactants include for example alkali metal or ammonium salts of acid sulfuric esters of addition products of ethylene oxide and/or propylene oxide with fatty alcohols, alkali metal or ammonium salts of alkylbenzenesulfonic acid or of alkylphenol ether sulfates. Products of the kind mentioned are commercially available. For example, the sodium salt of an acid sulfuric ester of a $C_{13}/C_{15}$ oxo process alcohol reacted with 106 mol of ethylene oxide, the triethanolamine salt of dodecylbenzenesulfonic acid, the sodium salt of alkylphenol ether sulfates and the sodium salt of the acid sulfuric ester of a reaction product of 106 mol of ethylene oxide with 1 mol of tallow fat alcohol are useful commercially available anionic surfactants. Useful anionic surfactants further include acid sulfuric esters of $C_{13}/C_{15}$ oxo process alcohols, paraffinsulfonic acids such as $C_{15}$-alkylsul-fonate, alkyl-substituted benzenesulfonic acids and alkyl-substituted naphthalenesulfonic acids such as dodecylbenzenesulfonic acid and di-n-butyl-naphthalenesulfonic acid and also fatty alcohol phosphates such as $C_{15}/C_{18}$ fatty alcohol phosphate. The polymerizable aqueous mixture can comprise combinations of a nonionic surfactant and an anionic surfactant or combinations of nonionic surfactants or combinations of anionic surfactants. Even cationic surfactants are suitable. Examples thereof are the dimethyl sulfate quaternized reaction products of 6.5 mol of ethylene oxide with 1 mol of oleylamine, distearyldimethylammonium chloride, lauryltrimethylammonium chloride, cetylpyridinium bromide and dimethyl sulfate quaternized triethanolamine stearate, which is preferably used as a cationic surfactant.

The amount of surfactant, based on the unneutralized monomer a) is preferably 0.01 to 10% by weight, more preferably 0.1 to 6% by weight, most preferably 0.8 to 3% by weight.

The polymerizable aqueous mixtures may optionally comprise at least one solubilizer g) as a further component. Solubilizers are water-miscible organic solvents, for example dimethyl sulfoxide, dimethylformamide, N-methylpyrrolidone, monohydric alcohols, glycols, polyethylene glycols or monoethers derived therefrom, subject to the proviso that the monoethers do not comprise any double bonds in the molecule. Useful ethers include methylglycol, butylglycol, butyldiglycol, methyldiglycol, butyltriglycol, 3-ethoxy-1-propanol and glycerol monomethyl ether.

When solubilizers g) are used, they are preferably included in the aqueous mixture at up to 50% by weight, more preferably in the range from 1% to 25% by weight and most preferably in the range from 5% to 10% by weight.

The aqueous mixture may optionally comprise thickeners, foam stabilizers, fillers, fibers and/or cell nucleators h). Thickeners are used for example to optimize foam structure and to improve foam stability. As a result, the foam will shrink only minimally during the polymerization. Useful thickeners include all natural and synthetic polymers known for this purpose that substantially increase the viscosity of an aqueous system and do not react with the amino groups of the basic polymers. The synthetic and natural polymers in question can be swellable or soluble in water.

An exhaustive overview of thickeners may be found for example in the publications by R. Y. Lochhead and W. R. Fron, Cosmetics & Toiletries, 108, 95-135 (May 1993) and M. T. Clarke, "Rheological Additives" in D. Laba (ed.) "Rheological Properties of Cosmetics and Toiletries", Cosmetic Science and Technology Series, Vol. 13, Marcel Dekker Inc., New York 1993.

Water-swellable or water-soluble synthetic polymers useful as thickeners include for example high molecular weight polyethylene glycols or copolymers of ethylene glycol and propylene glycol and also high molecular weight polysaccharides such as starch, guar flour, locust bean flour or derivatives of natural substances such as carboxymethylcellulose, hydroxyethylcellulose, hydroxymethylcellulose, hydroxypropylcellulose and mixed cellulose ethers. A further group of thickeners are water-insoluble products, such as finely divided silica, zeolites, bentonite, cellulose powders and other finely divided powders of crosslinked polymers. The aqueous mixtures may comprise the thickeners in amounts up to 30% by weight. When such thickeners are used at all, they are included in the aqueous mixture in amounts of 0.1%, preferably 0.5% up to 20% by weight.

To optimize foam structure, the aqueous reaction mixture may be admixed, if appropriate, with hydrocarbons having at least 5 carbon atoms in the molecule. Useful hydrocarbons include for example pentane, cyclopentane, hexane, cyclohexane, heptane, octane, isooctane, decane and dodecane. The contemplated aliphatic hydrocarbons can be straight-chain, branched or cyclic and have a boiling temperature which is above the temperature of the aqueous mixture during foaming. The aliphatic hydrocarbons extend the pot life of the foamed aqueous reaction mixture which has not yet polymerized. This facilitates the handling of the foams which have not yet polymerized and increases process consistency. The hydrocarbons act for example as cell nucleators and also stabilize the foam which has already formed. In addition, they can effect a further foaming of the mixture in the course of the polymerization of the monomer foam. They can then also have the function of a blowing agent. Instead of hydrocarbons or in a mixture therewith, it is also possible to use optionally chorinated or fluorinated hydrocarbons as a cell nucleator and/or foam stabilizer, for example dichloromethane, trichloromethane, 1,2-dichloro-ethane, trichlorofluoromethane or 1,1,2-trichlorotrifluoroethane. When hydrocarbons are used, they are used for example in amounts from 0.1% to 20% by weight and preferably from 0.1% to 10% by weight, based on the polymerizable aqueous mixture.

To modify the properties of the foams, the polymerizable aqueous mixture may have added to it one or more fillers, for example chalk, talc, clay, titanium dioxide, magnesium oxide, aluminum oxide, precipitated silicas in hydrophilic or hydrophobic forms, dolomite and/or calcium sulfate. The particle size of the fillers is for example in the range from 10 to 1000 µm and preferably in the range from 50 to 850 µm. The fillers can be included in the polymerizable aqueous mixture in amounts up to 30% by weight.

The aqueous mixtures described above, which comprise the monomers a), urea b), crosslinker d), initiator e) and surfactant f) as mandatory components, are initially foamed. For example, an inert gas can be dissolved in the polymerizable aqueous mixture at a pressure of for example 2-400 bar and the mixture subsequently decompressed to atmospheric. Decompression from a nozzle produces a flowable foam. The polymerizable aqueous mixture can also be foamed by another method, namely by dispersing fine bubbles of an inert gas in the polymerizable aqueous mixture. The foaming of the polymerizable aqueous mixture on a laboratory scale can be effected for example by foaming the aqueous mixture in a kitchen processor equipped with a whisk. Foaming is preferably carried out in an inert gas atmosphere and with inert gases, for example by mixing with nitrogen or noble gases under atmospheric or superatmospheric pressure, for example up to 25 bar, followed by decompression. The consistency of the foams, the size of the gas bubbles and the distribution of the gas bubbles in the foam can be varied within wide limits, for example through the choice of surfactants f), solubilizers g), foam stabilizers, cell nucleators, thickeners and fillers h). As a result, the density, the open-cell content of the foam and the wall thickness of the foam are readily adjustable to specific values. The aqueous mixture is preferably foamed at temperatures which are below the boiling point of the constituents of the aqueous mixture, for example in the range from room temperature to 100° C. and preferably in the range from 20 to 50° C. However, the aqueous mixture can also be foamed at temperatures above the boiling point of the component having the lowest boiling point by foaming the mixture in a pressuretightly sealed container. Foamed mixtures are obtained which are flowable and stable for a prolonged period. The density of the foamed mixture is for example in the range from 0.01 to 0.9 g/cm$^3$ at 20° C.

As usual for any type of polymeric foams, it is convenient to bring the foamed mixture into the shape desired for the superabsorbent foam. For example, to produce a superabsorbent foam sheet or roll-good, the foamed mixture is spread on a suitable support, such as a continuous belt of a belt-type polymerization and/or drying apparatus, by usual means, such as a blade-coater or a slit nozzle used for foaming by decompression. The desired thickness of the foam can easily be set in this step. It is also possible to fill moulds with foam for polymerization.

The foamed mixture is subsequently polymerized. The polymerization is carried out in the presence of customary radical-forming initiators. This gives crosslinked polymers which are superabsorbent. The radicals can be generated for example by heating (thermal polymerization) or by irradiation with light of a suitable wavelength (UV polymerization).

In accordance with the process of the present invention, superabsorbent foams having a layer thickness of up to about 5 millimeters are producible for example by unilateral or bilateral heating or in particular by unilateral or bilateral irradiation of the foamed polymerized or polymerizable aqueous mixture. When thicker superabsorbent foams are to be produced, for example foams several centimeters in thickness, it is particularly advantageous to heat the foamed material by means of microwaves, since relatively uniform heating can be achieved in this way. In this case, the thermal polymerization is effected for example at temperatures in the range from 20 to 140° C., preferably in the range from 40° C. to 120° C., more preferably in the range from 60 to 110° C. and most preferably in the range from 80 to 100° C. In the case of thicker foams, the foamed mixture is heat-treated on both surfaces, for example using contact heating or by irradiation or in a drying cabinet. The polymeric foams are open celled. The open cell content is for example at least 80% and preferably above 90%. Particular preference is given to foams having an open cell content of 100%. The open cell content of a foam is determined using scanning electron microscopy for example.

After the polymerizing of the foamed mixture or during the polymerizing, the hydrogel foam is dried. This removes water and other volatile constituents from the crosslinked hydrogel foam. Examples of suitable drying processes are thermal convection drying such as forced air drying, thermal contact drying such as roll drying, radiation drying such as infrared drying, dielectric drying such as microwave drying and freeze drying. The drying temperatures are typically in the range of 50 to 200° C., preferably 60 to 150° C., more preferably 80 to 120° C., most preferably 90 to 110° C. The preferred residence time at this temperature in the drier is preferably at least 1 minute, more preferably at least 2 minutes, most preferably at least 5 minutes, and typically at most 20 minutes. In order to avoid undesired decomposition and crosslinking reactions, it may be advantageous to perform the drying under reduced pressure, under a protective gas atmosphere and/or under gentle thermal conditions, under which the product temperature does not exceed 120° C., preferably 100° C. A particularly suitable drying process is (vacuum) belt drying.

Polymerization and/or drying are advantageously controlled such that the added blowing agent, i.e., the compound that is capable of thermal decomposition, undergoes thermal decomposition to some extent at least. To this end, the foamed or polymerized mixture is heated to temperatures of preferably at least 80° C., more preferably at least 90° C. and most preferably at least 100° C. in at least one step during its production.

Individual or all drying steps in the process according to the invention are preferably carried out at reduced pressure, i.e. a pressure below atmospheric pressure, preferably at less than 500 mbar and more preferably at less than 200 mbar, and are optionally augmented by means of a dry stream of gas, preferably nitrogen, at a rate in the range from 20 to 10001/kgh and preferably in the range from 100 to 2501/kgh, based on the mass of product to be dried.

After the drying step, the superabsorbent foam will usually comprise less than 10% by weight of water. However, the water content of the foam can be adjusted to any desired value by moistening with liquid water or water vapor. The water content of the superabsorbent foam is usually in the range from 1% to 60% by weight and preferably in the range from 2% to 10% by weight. The water content can be used to adjust the flexibility of the foam. Completely dried superabsorbent foams are harsh and brittle, whereas foamed materials having a water content of 5-20% by weight for example are flexible.

Foams producible by the process according to the present invention exhibit a distinctly increased swell rate. Curves plotting the uptake of liquid against time have a steep gradient. A water uptake equal to 50%, 80% or 90% of the free swell capacity of the superabsorbent foam is reached very quickly.

In a preferred embodiment of the present invention, the foam properties are enhanced through the formation of complexes on the surface. Complexes are formed on the foam by treating with at least one complexing agent. A complexing agent is an agent that comprises complexing cations. Preferably, this is effected by spraying with solutions of bi- or more highly valent cations, the cations being capable of reacting with functional groups, for example the acid groups, of the polymeric foam to form complexes. Examples of bi- or more highly valent cations are polymers that, formally, are wholly or partly constructed from vinylamine monomers, such as partially or fully hydrolyzed polyvinylamide (so-called "polyvinylamine"), whose amine groups are always—even at very high pH values—partly present in a state of protonation to ammonium groups, or metal cations, such as $Mg^{2+}$, $Ca^{2+}$, $Al^{3+}$, $Sc^{3+}$, $Ti^{4+}$, $Mn^{2+}$, $Fe^{2+}$, $Fe^{2+/3+}$, $Co^{2+}$, $Ni^{2+}$, $Cu^{2+}$, $Zn^{2+}$, $Y^{3+}$, $Zr^{4+}$, $La^{3+}$, $Ce^{4+}$, $Hf^{4+}$ and $Au^{3+}$. Preferred metal cations are $Mg^{2+}$, $Ca^{2+}$, $Al^{3+}$, $Ti^{4+}$, $Zr^{4+}$ and $La^{3+}$, and particularly preferred metal cations are $Al^{3+}$, $Ti^{4+}$ and $Zr^{4+}$. The metal cations can be used not only alone but also in admixture with each other. The anions are not subject to any fundamental restriction; of the metal cations mentioned, all metal salts that possess sufficient solubility in the solvent to be used are suitable. Metal salts with weakly complexing anions, for example chloride, nitrate and sulfate, bisulfate, carbonate, bicarbonate, nitrogen, phosphate, hydrogenphosphate, dihydrogenphosphate and carboxylate, such as acetate and lactate, are particularly suitable. It is particularly preferred to use aluminum sulfate $Al_2(SO_4)_3$. Useful solvents for the metal salts include water, alcohols, dimethylformamide, dimethyl sulfoxide and also mixtures thereof. Particular preference is given to water and water/alcohol mixtures, such as water/methanol, water/1,2-propanediol and water/1,3-propanediol. Water is very particularly preferred.

The concentration of the multivalent metal ion in the aqueous solution is generally at least 1% by weight, preferably at least 2% by weight and also generally not more than 20% by weight and preferably not more than 10% by weight. The amount of the multivalent metal ion used is generally at least 0.05% by weight, preferably at least 0.1% by weight and more preferably at least 0.2% by weight, for example at least 0.8% by weight, and also generally not more than 10% by weight, preferably not more than 8% by weight and more preferably not more than 5% by weight, for example not more than 3.2% by weight, based on the dry foam prior to application of the complexing agent. A foam is "dry" for the purposes of this invention when its water content is not more than 5% by weight. When aluminum sulfate is used, a cation content of 0.8% by weight corresponds to an $Al_2(SO_4)_3$ content of 5% by weight and a cation content of 3.2% by weight corresponds to an $Al_2(SO_4)_3$ content of 20% by weight.

The complexing agents to be applied are applied to the foam as described, preferably as a solution or, if insoluble, as a dispersion or solid.

The surface complexing step is optionally followed by drying. Drying can be effected in a conventional manner, say by heating the shell of the reaction apparatus or by blowing hot air into the reaction apparatus. It is similarly possible to use a downstream dryer as also used to dry the unaftertreated foam. Preferred drying temperatures range from 50 to 250° C., preferably from 50 to 200° C. and more preferably from 50 to 150° C. The residence time at this temperature in the dryer is advantageously below 30 minutes and preferably below 20 minutes.

The foams according to the present invention may optionally be surface post-crosslinked Postcrosslinkers suitable for this purpose are compounds that comprise at least two groups that are capable of forming covalent bonds with the carboxylate groups of the composite. Useful compounds include for example alkoxysilyl compounds, polyaziridines, polyamines, polyamidoamines, di- or polyepoxides, as described in EP 83 022 A2, EP 543 303 A1 and EP 937 736 A2, di- or polyfunctional alcohols, as described in DE 33 14 019 A1, DE 35 23 617 A1 and EP 450 922 A2, or β-hydroxyalkylamides, as described in DE 102 04 938 A1 and U.S. Pat. No. 6,239,230.

Postcrosslinking is typically carried out by spraying the foam with a solution of the post-crosslinker. But it is also possible to dip the foam into a solution of the postcrosslinker. Subsequently, the foam is thermally dried, and the crosslinking reaction can take place not only before but also during drying. The drying temperatures are typically in the range of 100 to 250° C., preferably 120 to 220° C., more preferably 130 to 210° C., most preferably 150 to 200° C. The preferred residence time at this temperature in the drier is preferably at least 10 minutes, more preferably at least 20 minutes, most preferably at least 30 minutes, and typically at most 60 minutes. In order to avoid undesired decomposition and crosslinking reactions, it may be advantageous to perform the drying under reduced pressure, under a protective gas atmosphere and/or under gentle thermal conditions, under which the product temperature does not exceed 120° C., preferably 100° C. A particularly suitable drying process is (vacuum) belt drying.

To improve the properties, the polymeric foams can additionally be coated or remoisturized, or other additives may be added.

Suitable coatings for improving the speed of liquids absorption and the liquids permeability in the foam are, for example, inorganic inert substances, such as water-insoluble metal salts, organic polymers, cationic polymers and di- or polyvalent metal cations, such as aluminum sulfate and aluminum lactate. Suitable coatings for counteracting the undesired caking tendency are, for example, fumed silica, such as Aerosil® 200, and surfactants, such as Span® 20.

Suitable additives for reducing the content of unconverted monomers (residual monomers) are, for example, reducing agents such as the salts of sulfurous acid, of hypophosphorous acid and/or of organic sulfinic acid. Preferable reducing agents are sodium disulfite ($Na_2S_2O_5$) or a mixture of the sodium salt of 2-hydroxy-2-sulfinatoacetic acid, the disodium salt of 2-hydroxy-2-sulfonatoacetic acid and sodium hydrogensulfite. Such mixtures are available as Brüggolite® FF6 and Brüggolite® FF7 (Brüggemann Chemicals; Heilbronn; Germany). If used, these reducing agents are typically added in amounts of at least 0.01% by weight, preferably at least 0.5% by weight and more preferably at least 1% by weight and of not more than 5% by weight, preferably not more than 4% by weight and more preferably not more than 3% by weight, based on the weight of dry foam. 2 to 2.5% by weight of sodium disulfite, for example 2.25% by weight, will provide sufficient residual monomer reduction in most cases. These additives may be added at any suitable stage in the process, for example during or after the surface complexing, surface crosslinking or additional coating steps.

The optionally surface-postcrosslinked superabsorbent foam produced by the process according to the present invention can be used for all the purposes which for example the superabsorbent hydrogel foams which are known from EP 858 478 B1 and which are based on polymers comprising acid groups, such as on crosslinked polyacrylates. The foams of the present invention can be useful for example in hygiene articles for absorbing body fluids.

In a further preferred embodiment, the superabsorbent foam can be additionally reinforced by means of a web. To this end, the foamed mixture is brought into contact with the web prior to polymerization.

Webs are nonwoven articles of manufacture which are composed of fibers and whose integrity is generally due to the intrinsic clingingness of the fibers. Webs are preferably consolidated mechanically, for example by needling, interlooping or entangling by means of sharp jets of water or air. Webs can also be consolidated adhesively or cohesively. Adhesively consolidated webs are obtainable for example by interadhering the fibers with liquid binders or by melting binder fibers which are added to the web in the course of its production. Cohesively consolidated webs are producible for example by incipiently dissolving the fibers with suitable chemicals and applying pressure.

Examples of synthetic fibers are fibers composed of polyethylene, polypropylene, polybutylene terephthalate, polyamide, polyethylene terephthalate, polyester, polysulfone and/ or polyether ketone. It is also possible to use fibers composed of carbon or glass fibers. Polyester webs are particularly preferred.

The basis weight of the webs is preferably not more than 150 g/m², more preferably in the range from 5 to 100 g/m² and most preferably in the range from 8 to 40 g/m².

The thickness of the webs is preferably in the range from 0.01 to 2 mm, more preferably in the range from 0.01 to 1.0 mm and most preferably in the range from 0.05 to 0.5 mm.

Either the monomer foam can be added to a web previously placed on a suitable support, or a web can be placed on a monomer foam previously applied to a suitable support. But it is also possible first to apply a portion of the monomer foam to a suitable support, place the web on top and subsequently add the rest of the monomer foam. For example, the foam can be knife-coated onto the support in the desired thickness. The support has advantageously been provided with an antistick coating.

Advantageously, the amount of monomer foam is chosen such that the monomer foam is completely penetrated by the web, i.e., the monomer foam preferably extends to less than 20% beyond the web, more preferably to less than 10% and most preferably to less than 5%, all based on the total thickness of the foam. This enhances the stability of the present invention's foams in the swollen state.

Use of the webs gives superabsorbent foams which, on contact with water or aqueous fluids, will now only swell one-dimensionally, i.e., swelling takes the form of a change in the thickness and not the area of the foams.

The present invention further provides feminine hygiene absorbent articles comprising superabsorbent foams which are producible by the process according to the present invention and also superabsorbent foams having a free swell capacity (FSC, method of measurement described hereinbelow in the "Methods of determination" section) of at least 10 g/g, preferably at least 20 g/g, more preferably at least 30 g/g and most preferably in the range from 40 to 100 g/g, with 90% of the free swell capacity being reached in not more than 30 seconds, preferably not more than 25 seconds, more preferably not more than 20 seconds and most preferably not more than 15 seconds.

The thickness of the foam in a form suitable for most purposes can be typically in the range from 0.05 to 4 mm, preferably in the range from 0.25 to 2.5 mm, more preferably in the range from 0.5 to 1.5 mm and most preferably in the range from 0.6 to 0.9 mm.

According to the present invention, the feminine hygiene absorbent article can comprise the superabsorbent foam as described above typically in the absorbent core as it is known in the art, for example as a layer of desired shape and thickness, or also as a composite structure comprising a layer of the superabsorbent foam and other layers, e.g. fibrous layers. The superabsorbent foam can be comprised in a feminine hygiene absorbent article according to the present invention in addition or as an alternative to traditional superabsorbent polymers or absorbent gelling materials.

The superabsorbent foam can be comprised in the feminine hygiene absorbent article according to the present invention in an amount of 0.1 g to 20 g, or of 0.15 g to 15 g, or of 0.2 g to 10 g, or also of 0.3 g to 5 g. For example, the superabsorbent foam can be comprised in the feminine hygiene article of the present invention as a layer or a combination of layers in an overall amount as specified above.

The superabsorbent foam can be also provided in the selected amount, typically for example in the core of a feminine hygiene absorbent article of the present invention, in the form of a plurality of pieces of selected size, for example particles, which can be obtained with means known in the art, for example cutting or comminuting larger foam pieces in order to obtain the smaller pieces having the desired size. Said smaller pieces of superabsorbent foam, for example particles, can be provided in a feminine hygiene absorbent article according to the present invention, for example typically in the absorbent core, in the selected amount as specified above. They can be for example distributed within a fibrous material, such as fluff pulp, or comprised in a layer between containing, e.g. fibrous, sheets, thus forming a laminate structure. The pieces, for example particles, can typically have a mean particle size from 100 to 1000 µm, or from 250 to 600 µm, or also from 300 to 500 µm. The mean particle size of the particles may be determined by means of EDANA recommended test method No. WSP 220.2-05 "Particle size distribution", where the proportions by mass of the screen fractions are plotted in cumulated form and the mean particle size is determined graphically. The mean particle size here is the value of the mesh size which gives rise to a cumulative 50% by weight.

The amount of the superabsorbent foam can be evaluated, typically in a feminine hygiene absorbent product containing it, and particularly when it is comprised in particle form, with any suitable method, such as for example by means of a superabsorbent polymer titration method, as it is known to the skilled person.

In the feminine hygiene absorbent article according to the present invention the core may be generally selected from any of the absorbent cores or core systems known in the art. As used herein the term absorbent core refers to any material or multiple material layers whose primary function is to absorb, store and distribute fluid.

For example, the absorbent core can include the following components: (a) an optional fluid distribution layer for example comprising a primary fluid distribution layer together with a secondary fluid distribution layer; (b) a fluid storage layer; (c) an optional fibrous ("dusting") layer underlying the storage layer; and (d) other optional components. According to the present invention, the superabsorbent foam can be provided in at least one of said layers, for example in the fluid storage layer. For example, the superabsorbent foam can be comprised in the storage layer of such a composite core construction, comprised between a fibrous primary fluid distribution layer and a fibrous dusting layer. The superabsorbent foam can for example be comprised as a layer entirely constituting the storage layer in such a composite core structure. In an alternative embodiment similar to that described above the superabsorbent foam can be incorporated in form of a plurality of pieces, for example in particle form, typically with the selected particle size, between suitable fibrous layers which in turn can constitute the fluid distribution layer and the dusting layer. In all embodiments of the present invention, such as those described above, the superabsorbent foam can be typically incorporated in the selected amount specified above.

The superabsorbent foams for use in accordance with the invention have a high absorption capacity for blood and a high free swell rate, and are therefore particularly suitable for use in feminine hygiene articles for absorption of menses, vaginal secretions, as well as urine.

This is particularly desirable as traditional superabsorbent materials may in comparison have less than optimal absorption and retention capacity towards body fluids such as menses and vaginal secretions due to the viscosity and/or complex nature of these fluids. Menses and vaginal secretions are in fact water based fluids comprising components having molecular weights higher than water and also corpuscular components, including red cells, white cells, soluble proteins, cellular debris and mucus, which slow down the absorption of these fluids by superabsorbents. Menses and vaginal secretions are rather thick, and more difficult to absorb in absorbent structures with conventional absorbent gelling materials; moreover, corpuscular components like red cells may decrease the absorption capacity of certain superabsorbent particles. This translates into a slower initial uptake rate of the fluid into the superabsorbent material, and in turn in the absorbent article comprising the superabsorbent material, which can result in a lower final absorption and retention capacity.

Feminine hygiene absorbent articles of the present invention have hence an improved absorption and retention of menses, vaginal secretions or urine.

Methods:

Measurements should unless otherwise stated be carried out at an ambient temperature of 23±2° C. and a relative humidity of 50±10%.

Free Swell Capacity (FSC)

The free swell capacity of the superabsorbent foam is determined similarly to the "Absorption under Pressure" as per DIN ISO 17190-7. A superabsorbent foam is tested instead of the water-absorbing polymeric particles. To this end, a circular sample 25 mm in diameter is die-cut out of the foam. The measurement is carried out pressurelessly in that no plunger is placed on the sample.

Centrifuge Retention Capacity (CRC)

The centrifuge retention capacity of the superabsorbent foam is determined as per DIN ISO 17190-6. A superabsorbent foam is tested instead of the water-absorbing polymeric particles.

Free Swell Time ($t_{FSCx\ s}$)

The free swell time is measured in accordance with the method indicated above for determining the free swell capacity (FSC) except that the amount of liquid taken up is recorded against time. The free swell time is the time needed to absorb an amount of liquid equal to x % of the free swell capacity (FSC).

Wet Failure Value

The wet failure value is determined as per the method described in WO 2004/035668 A2 at page 30 line 29 to page 31 line 26.

EXAMPLES

The examples according to the invention describe exemplary superabsorbent foams which can be comprised in feminine hygiene absorbent articles of the present invention, typically for example in the absorbent core.

Comparative Example

A magnetic stirrer was used to mix the following components together in a glass beaker:
209.13 g of acrylic acid
81.31 g of 37.3% sodium acrylate solution in water
16.8 g of polyethylene glycol diacrylate 400
25.60 g of 15% aqueous solution of an addition product of 80 mol of ethylene oxide onto 1 mol of a linear saturated $C_{16}$-$C_{18}$ fatty alcohol
26.62 g of water This solution was gradually admixed with 240.54 g of triethanolamine with ice cooling, followed by allowing to cool to 15° C. The solution obtained was transferred into a pressure vessel and saturated therein with carbon dioxide at a pressure of 12 bar for 25 minutes by passing a 300 l/h carbon dioxide stream through the solution. Under pressure, 16 g of a 3% by weight aqueous solution of 2,2'-azobis(2-amidinopropane)dihydrochloride were added and subsequently carbon dioxide was passed through the reaction mixture for a further 5 minutes. The reaction mixture was then expressed at a pressure of 12 bar through a die 1.0 mm in diameter to form a free-flowing fine-cell foam.

The monomer foam obtained was applied to an A3 size glass plate having rims 3 mm high, and was covered with a second glass plate. The foam sample was irradiated simultaneously from both sides with UV light for 4 minutes, from above with a UVASPOT 1000/T UV/VIS radiator from Dr. Hönle AG, Gräfelfing, Germany, from below with 2 UVASPOT 400/T UV/VIS radiators from the same manufacturer, during which the temperature rose to about 120° C.

The foam layer obtained was fully dried under a stream of nitrogen and subsequently adjusted to a moisture content of 5% by weight by spraying with water.

Solids content of reaction mixture: 81.35%
Degree of neutralization: 60 mol %
Monomer foam density: 0.24 gcm$^{-3}$
Foam structure: homogeneous, fully open-cell, no skin The properties of the superabsorbent foam are reported in Table 1.

Examples 1 to 7

The comparative example was repeated using a monomer solution comprising 1% to 30% by weight of urea, based on acrylic acid. The superabsorbent foam obtained was dried at 80° C.

The properties of the superabsorbent foam are reported in Table 1.

TABLE 1

| | Urea content | | | | | |
|---|---|---|---|---|---|---|
| Ex. | Urea content | FSC | CRC | $t_{FSC50\%}$ | $t_{FSC80\%}$ | $t_{FSC90\%}$ |
| Comp. | 0% | | | 27 s | 33 s | 36 s |
| 1 | 1% | 45 g/g | 6.9 g/g | 17 s | 21 s | 23 s |
| 2 | 5% | 50 g/g | 6.6 g/g | 9 s | 12 s | 14 s |
| 3 | 10% | 49 g/g | 7.2 g/g | | | |
| 4 | 15% | 35 g/g | 6.8 g/g | | | |
| 5 | 20% | 50 g/g | 6.9 g/g | | | |
| 6 | 25% | 39 g/g | 6.3 g/g | | | |
| 7 | 30% | 35 g/g | 5.2 g/g | | | |

Examples 8 to 13

The comparative example was repeated using a monomer solution comprising 5% by weight of urea, based on acrylic acid. The superabsorbent foam obtained was dried at 70 to 150° C.

The properties of the superabsorbent foam are reported in Table 2.

TABLE 2

| | Drying temperature | | | | | |
|---|---|---|---|---|---|---|
| Ex. | Drying temperature | FSC | CRC | $FSCt_{50\%}$ | $FSCt_{80\%}$ | $FSCt_{90\%}$ |
| 8 | 70° C. | 49 g/g | 7.4 g/g | | | |
| 2 | 80° C. | 50 g/g | 6.6 g/g | 9 s | 12 s | 14 s |
| 9 | 90° C. | 47 g/g | 7.1 g/g | | | |
| 10 | 110° C. | 39 g/g | 5.1 g/g | | | |
| 11 | 120° C. | 13 g/g | 1.8 g/g | | | |
| 12 | 130° C. | 16 g/g | 2.5 g/g | 6 s | 8 s | 8 s |
| 13 | 150° C. | 14 g/g | 1.9 g/g | | | |

Examples 14 to 17

The comparative example was repeated using a monomer solution comprising 1% to 20% by weight of urea, based on acrylic acid. The superabsorbent foam obtained was dried at 130° C.

The properties of the superabsorbent foam are reported in Table 3.

TABLE 3

| | Urea content | | | | | |
|---|---|---|---|---|---|---|
| Ex. | Urea content | FSC | CRC | $t_{FSC50\%}$ | $t_{FSC80\%}$ | $t_{FSC90\%}$ |
| Comp. | 0% | 21 g/g | 3.0 g/g | | | |
| 14 | 1% | 19 g/g | 2.9 g/g | | | |
| 12 | 5% | 16 g/g | 2.5 g/g | 6 s | 8 s | 8 s |
| 15 | 10% | 12 g/g | 1.4 g/g | | | |
| 16 | 15% | 11 g/g | 1.8 g/g | | | |
| 17 | 20% | 17 g/g | 2.0 g/g | | | |

Examples 18 and 19

The superabsorbent foams of Example 2 were additionally sprayed with, respectively, 5% and 10% by weight of aluminum sulfate, based on the foam.

The properties of the coated foam are reported in Table 4.

TABLE 4

| Coating with aluminum sulfate | | |
|---|---|---|
| Example | Aluminum sulfate | Wet failure rate |
| 2 | none | 0.128 g/mm$^2$ |
| 18 | 5% | 0.345 g/mm$^2$ |
| 19 | 10 | 0.475 g/mm$^2$ |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A feminine hygiene absorbent article comprising a composite comprising a superabsorbent foam and a fibrous web layer,
    wherein the superabsorbent foam is obtainable by foaming an aqueous mixture comprising at least one polymerizable monoethylenically unsaturated monomer bearing acid groups, at least one polymerizable crosslinker and at least one surfactant, polymerizing the foamed mixture and drying the polymerized mixture, wherein the foamed mixture comprises at least 1% by weight, based on the monomer, of at least one compound capable of thermal decomposition with gas formation; wherein the compound capable of thermal decomposition with gas formation is urea;
    wherein the superabsorbent foam further comprises a coating;
    wherein the fibrous web layer is composed of synthetic fiber, has a basis weight of no more than 200 g/m² and a thickness of not more than 5 mm;
    wherein the synthetic fiber is selected from the group consisting of polyethylene, polypropylene, polybutylene terephthalate, polyamide, polyethylene terephthalate, polyester, polysulfone, and polyether ketone;
    wherein a full thickness of the fibrous web layer is completely penetrated by the superabsorbent foam such that the superabsorbent foam has an integral fibrous web support; and
    wherein the composite only swells one-dimensionally when in contact with an aqueous fluid such that the composite swells in a thickness direction while an area of the composite remains unchanged.

2. The feminine hygiene absorbent article of claim 1 wherein the polymerization is initiated by radiation.

3. The feminine hygiene absorbent article of claim 1 wherein the polymerization is carried out at a temperature of less than 110° C.

4. The feminine hygiene absorbent article of claim 1 wherein the drying is carried out at a temperature of less than 120° C.

5. The feminine hygiene absorbent article of claim 1 wherein the drying is carried out at a pressure below atmospheric pressure.

6. The feminine hygiene absorbent article of claim 1 wherein the acid groups of the monoethylenically unsaturated monomer are at least partly in a neutralized state.

7. The feminine hygiene absorbent article of claim 1 wherein the coating comprises at least one salt of a multivalent cation.

8. The feminine hygiene absorbent article of claim 1 wherein a water content of the superabsorbent foam is adjusted to a value between 1% and 60% by weight.

9. The feminine hygiene absorbent article of claim 1 wherein the superabsorbent foam has a free swell capacity of at least 10 g/g with 90% of the free swell capacity being reached in not more than 30 seconds.

10. The feminine hygiene absorbent article of claim 9 wherein said superabsorbent foam is 0.05 to 4 mm in thickness.

11. The feminine hygiene absorbent article according to claim 9 wherein the acid groups of the polymerized monoethylenically unsaturated monomer are at least partly in a neutralized state.

12. The feminine hygiene absorbent article of claim 9 wherein said coating comprises at least one salt of a multivalent cation.

13. The feminine hygiene absorbent article of claim 1, wherein said superabsorbent foam is provided in an amount of 0.1 g to 20 g.

14. The feminine hygiene absorbent article of claim 1, wherein said feminine hygiene absorbent article comprises a topsheet, a backsheet and an absorbent core disposed therebetween, wherein said absorbent core comprises said composite.

15. The feminine hygiene absorbent article of claim 14, wherein said feminine hygiene absorbent article is a sanitary napkin or a pantiliner.

16. The feminine hygiene absorbent article of claim 1, wherein the coating comprises of inorganic inert substances, organic polymers, cationic polymers and di- or polyvalent metal cations, fumed silica, surfactants, or combinations thereof.

* * * * *